United States Patent [19]

Komuro

[11] Patent Number: 5,035,017
[45] Date of Patent: Jul. 30, 1991

[54] MAGNETIC SLEEPING MAT
[75] Inventor: Mitsuo Komuro, Tokyo, Japan
[73] Assignee: Nippon Athletic Industry Company, Tokyo, Japan
[21] Appl. No.: 640,118
[22] Filed: Jan. 11, 1991
[51] Int. Cl.[5] .............................................. A47C 27/22
[52] U.S. Cl. .......................................... 5/481; 5/448; 600/9
[58] Field of Search ................... 5/448, 481, 420, 417; 600/9, 15

[56] References Cited

U.S. PATENT DOCUMENTS

| | | | |
|---|---|---|---|
| 4,143,435 | 3/1979 | Masuda | 5/481 |
| 4,330,892 | 5/1982 | Fukushima | 5/462 |
| 4,509,219 | 4/1985 | Yagi | 5/481 |
| 4,924,542 | 5/1990 | Yamaguchi | 5/481 |

FOREIGN PATENT DOCUMENTS 54-25109  2/1979  Japan ....................... 5/448

Primary Examiner—Alexander Grosz
Attorney, Agent, or Firm—Young & Thompson

[57] ABSTRACT

A magnetic sleeping mat having a magnetic effect and a manual pressure effect; comprising a foamed synthetic resin board having large projection formed on its upper surface and further having small projections on its upper surface and bottom surface; a first fibrous sheet having holes and superposed on the upper surface of the foamed synthetic resin board so as to be fitted in its holes with the large projections of the foamed synthetic resin board and to be contacted with the small projections of the board; a second fibrous sheet having holes and superposed on the upper surface of the first fibrous sheet so as to be fitted in its holes with the large projections of the board; permanent magnets arranged on the second fibrous sheet; and a cover cloth which covers the laminated assembly consisting of the foamed synthetic resin board, the first fibrous sheet and the second fibrous sheet containing the permanent magnets.

2 Claims, 5 Drawing Sheets

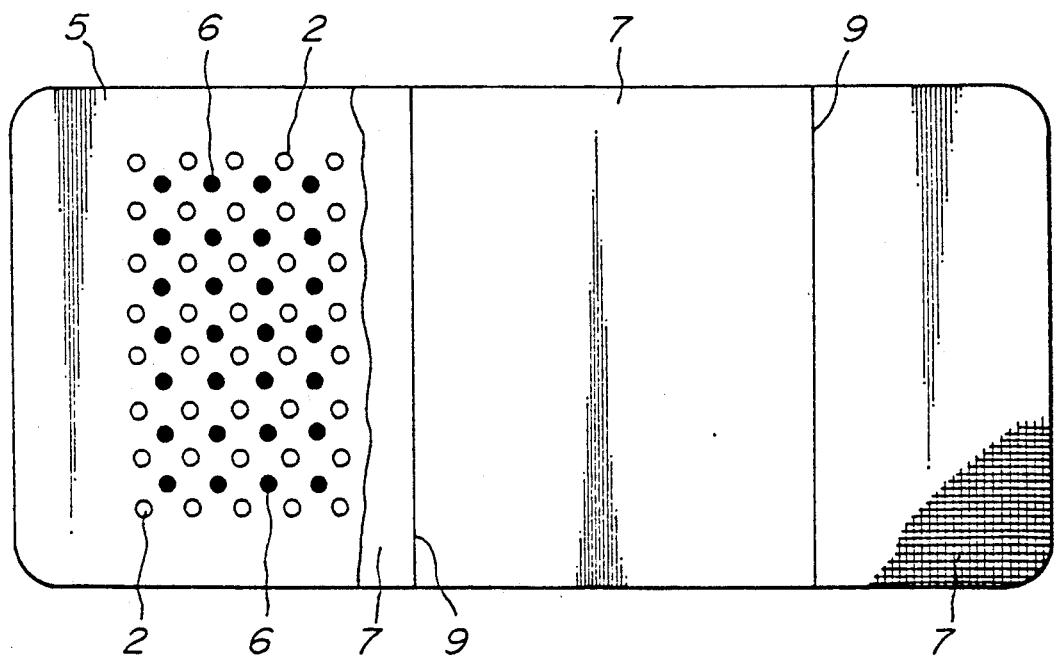
FIG_1

FIG_2
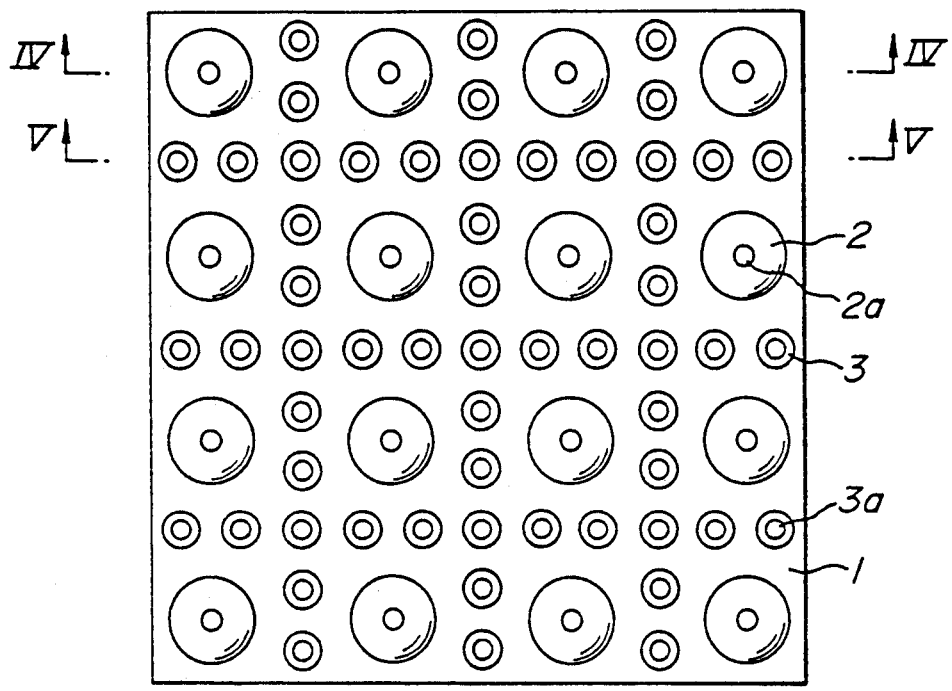
FIG_3
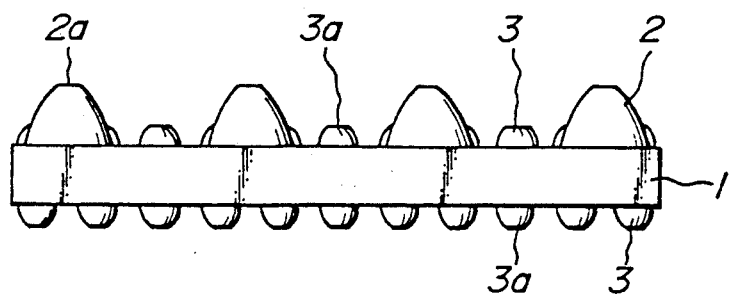

FIG._4
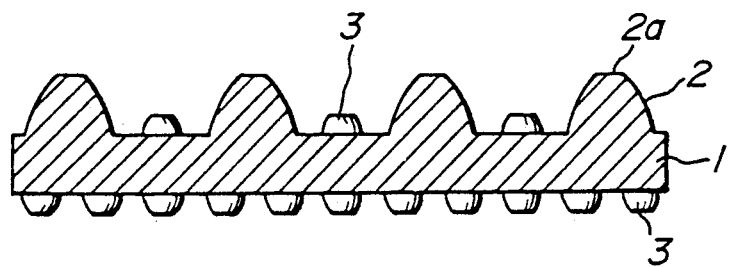
FIG._5
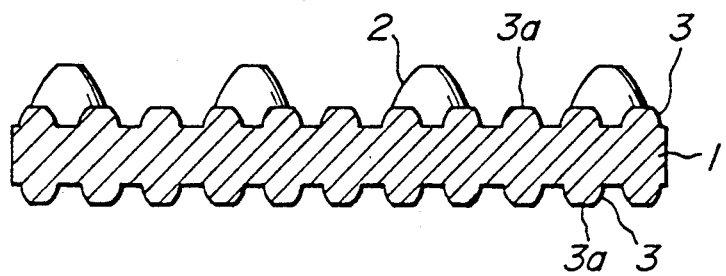
FIG._6
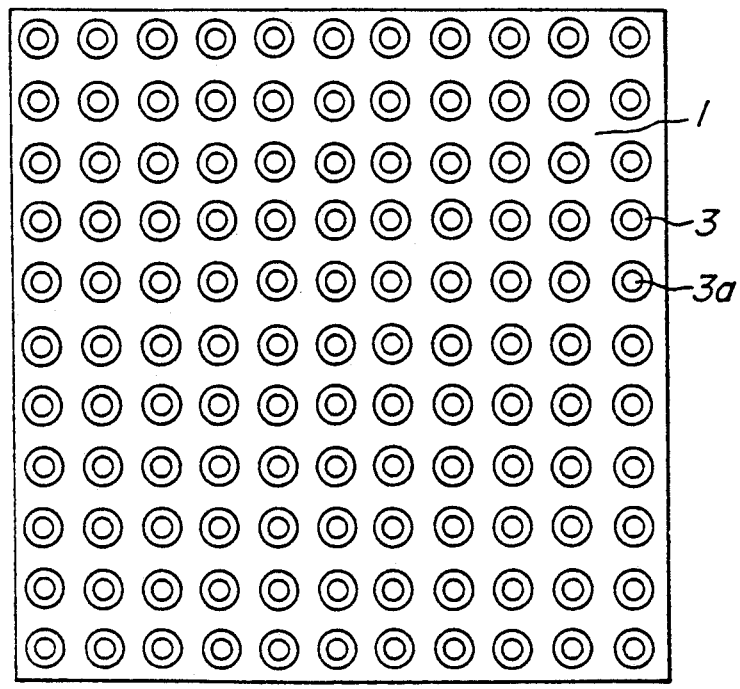

FIG._9
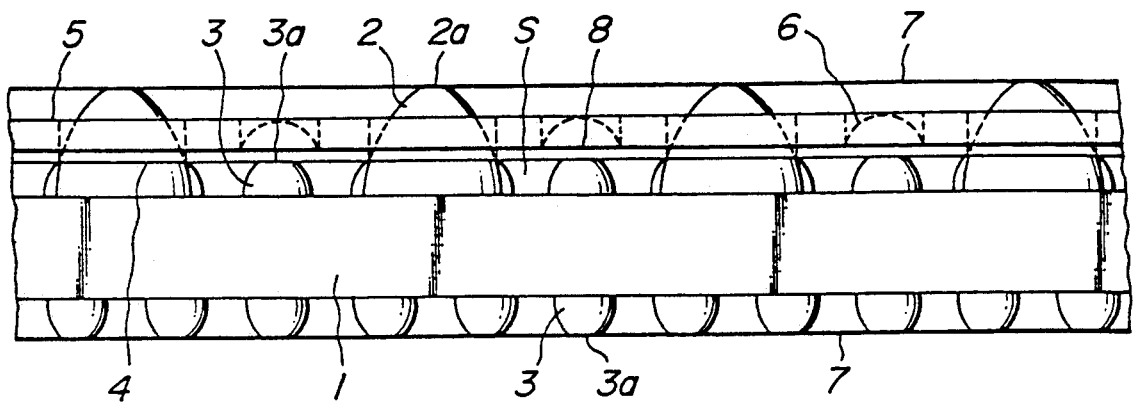
FIG._10
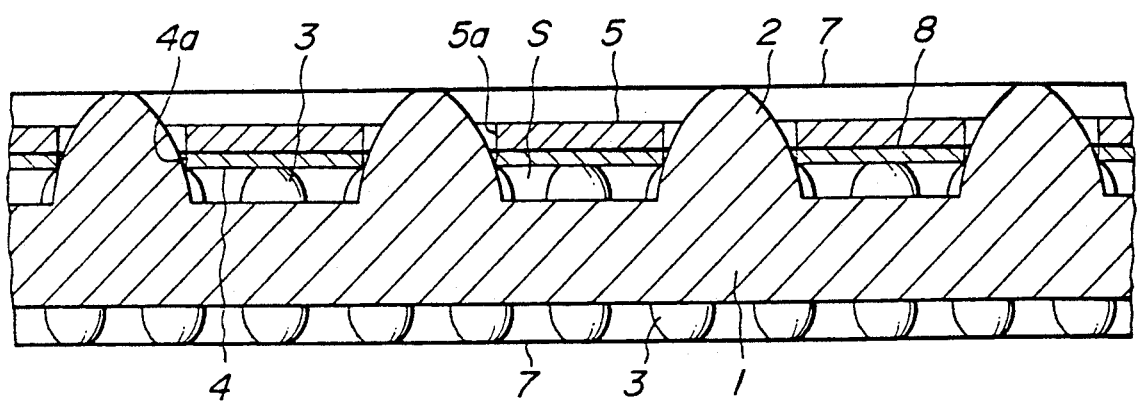
FIG._11
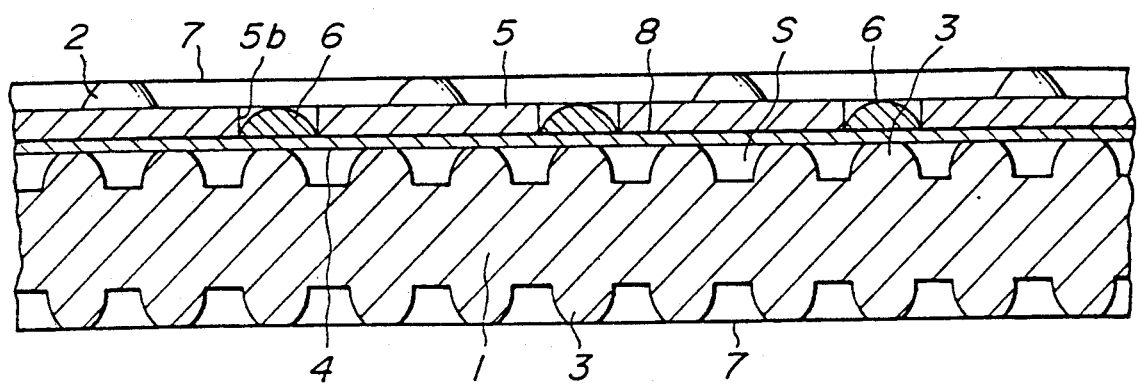

MAGNETIC SLEEPING MAT

BACKGROUND OF THE INVENTION

1. Field of the Invention

This invention relates to a magnetic sleeping mat having a magnetic effect, which is obtained by acting magnetic force of magnet to a human body, together with a manual pressure effect, which is obtained by press contacting the projections of the mat with the human body.

2. Related Art Statement

There have been proposed various magnetic sleeping mats having the above described magnetic effect and manual pressure effect in various publications, for example, in Japanese Utility Model Application Publication Nos. 55-44,534 and 61-27,486.

However, among these conventional magnetic sleeping mats of this kind, mats directed to magnetic effect have often rugged portions, and mats directed to a manual pressure effect give often a pain to the human body during the use due to the presence of locally formed uneven projections. Therefore, conventional magnetic sleeping mats have a problem that the mats are unsatisfactory in the comfortableness, such as heat insulation properties or the like, which is primarily required of bedclothes.

Moreover, there has not hitherto been produced a magnetic sleeping mat having both of satisfactorily excellent magnetic effect and manual pressure effect without deteriorating the comfortableness as bedclothes.

SUMMARY OF THE INVENTION

The object of the present invention is to provide a magnetic sleeping mat free from the above described drawbacks.

One of the features of the present invention lies in the provision of a magnetic sleeping mat, comprising a board consisting of a foamed synthetic resin; a first fibrous sheet superposed on the foamed synthetic resin board; a second fibrous sheet superposed on the first fibrous sheet; permanent magnets distributedly arranged on the second fibrous sheet; and a cover cloth which covers the laminated assembly consisting of the foamed synthetic resin board, the first fibrous sheet and the second fibrous sheet containing the permanent magnets; said foamed synthetic resin board having large projections, which are distributedly formed on its upper surface, and small projections, which are distributedly formed on its upper surface and are located between the large projections, and further having small projections which are distributedly formed on its bottom surface; said first fibrous sheet having holes, which have been formed therethrough, and being superposed on the upper surface of the foamed synthetic resin board so as to be fitted in its holes with the large projections of the foamed synthetic resin board and to be contacted with the top potions of the small projections thereof; and second fibrous sheet having holes, which have been formed therethrough, and being superposed on the upper surface of the first fibrous sheet so as to be fitted in its holes with the large projections of the foamed synthetic resin board.

Another feature of the present invention lies in the provision of a magnetic sleeping mat, wherein a cloth, which has previously been subjected to a heat insulation treatment or a radiation heat-reflection treatment, has been interposed between the lower first and upper second fibrous sheets in the above described magnetic sleeping mat.

BRIEF DESCRIPTION OF THE DRAWINGS

FIGS. 1 is a plan view, partly in section, of one embodiment of the magnetic sleeping mat of the present invention;

FIG. 2 is a plan view of a part of the interlining of the magnetic sleeping mat of the present invention;

FIG. 3 is a side view of the interlining illustrated in FIG. 2;

FIG. 4 is a cross-sectional view of the interlining illustrated in FIG. 2 in the arrow direction along the line IV—IV in FIG. 2;

FIG. 5 is a cross-sectional view of the interlining illustrated in FIG. 2 in the arrow direction along the line V—V in FIG. 2;

FIG. 6 is a view of the bottom surface of the interlining illustrated in FIG. 2;

FIG. 9 is a side view, in the arrow direction along the line IX—IX in FIG. 7, of a part of a magnetic sleeping mat of the present invention, which has been obtained by covering with a cover cloth the laminated assembly illustrated in FIG. 7 and having a cloth inserted between the first fibrous sheet and the second fibrous sheet;

FIG. 10 is a cross-sectional view of the magnetic sleeping mat illustrated in FIG. 9 in the allow direction along the line X—X in FIG. 7; and FIG. 11 is a cross-sectional view of the magnetic sleeping mat illustrated in FIG. 9 in the allow direction along the line XI—XI in FIG. 7.

DESCRIPTION OF THE PREFERRED EMBODIMENTS

One embodiment of the magnetic sleeping mat of the present invention will be explained referring to the accompanying drawings.

Figure 7:
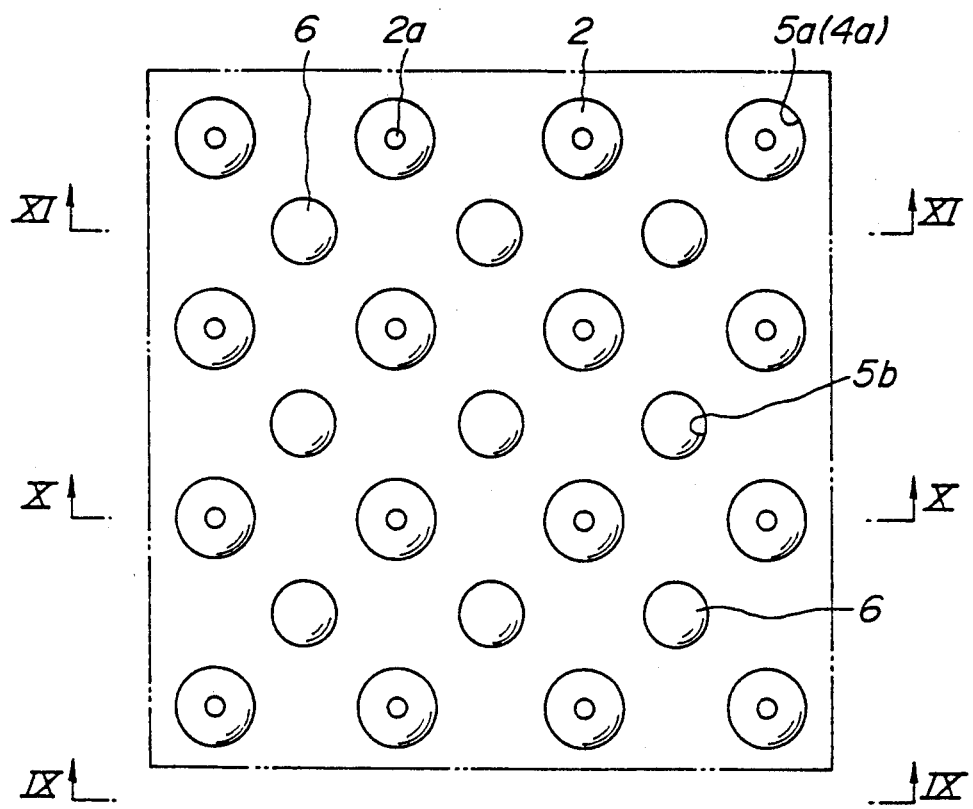
FIG. 7 is a plan view of a part of a laminated assembly obtained by superposing the first and second fibrous sheets on the interlining illustrated in FIG. 2.
Figure 8:
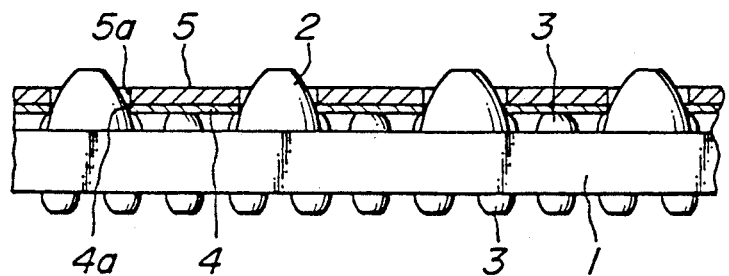
FIG. 8 is a side view, partly in section, of the laminated assembly illustrated in FIG. 7.

In this embodiment, as fragmentarily illustrated in FIGS. 2-6, a board 1 consisting of a foamed synthetic resin, such as foamed crosslinked polyethylene or the like, has large projections 2 distributedly formed on its upper surface, each large projection 2 having substantially a conical shape, and small projections 3 formed between the large projections 2 and distributed on the its upper surface, each small projection 3 having substantially a semi-spherical shape and having a height smaller than that of the large projections 2, and further has small projections 3 distributedly formed on its bottom surface, each small projection 3 having the same shape as that of the above described small projection 3 formed on the upper surface of the board 1. A first fibrous sheet 4 having holes 4a formed therethrough (referred to FIGS. 7, 8 and 10), which are to be fitted with the above described large projection 2 formed on the upper surface of the board 1, are superposed on the upper surface of the board 1 such that the first fibrous sheet 4 is contacted with the flat top portions 3a of the small projections 3 formed on the upper surface of the board 1 and is further fitted in its holes 4a with the large projections 2 of the board 1. Further, a second fibrous sheet 5 having holes 5a formed therethrough, which are to be fitted with the above described large projections 2, and further having magnet-receiving holes 5b distributedly formed thereon is superposed on the upper surface of the first fibrous sheet 4. A permanent magnet 6 is inserted into each of the magnet-receiving holes 5b. The resulting laminated assembly consisting of the superposed board 1, and first and second fibrous sheets 4 and 5 is covered with a cover cloth 7 to form a magnetic sleeping mat of the present invention. The numeral 2a represents the flat top portion of the large projection 2.

In another embodiment of the magnetic sleeping mat of the present invention, as illustrated in FIGS. 9-11, a cloth 8 made of nylon mesh or the like is arranged between the lower first fibrous sheet 4 and the upper second fibrous sheet 5, and permanent magnets 6 are fixed to the cloth 8. Further, when the cloth 8 is subjected to heat insulation treatment and radiation heat-reflection treatment by means of a vapor deposition of aluminum and the like, a magnetic sleeping mat having an improved heat insulating property can be obtained.

FIG. 1 is a whole plan view of the magnetic sleeping mat of the present invention, and the numeral 9 represents a dividing line or folding line formed in order to carry out easily the folding or housing of the sleeping mat.

As the above described first and second fibrous sheets 4 and 5, there can be used textile sheets made of various fibers, such as wool, synthetic fiber, and the like. Particularly, when wool felt is used as the upper second fibrous sheet 5, a magnetic sleeping mat having an improved comfortableness can be obtained because of the excellent heat insulating property and hygroscopicity of the wool felt.

The lower first fibrous sheet 4 does not directly contact with a human body, and hence there may be used inexpensive fibrous sheets, such as synthetic fiber felt, hard cotton felt and the like.

The magnetic sleeping mat according to the present invention has the above described structure, and hence the top portions 2a of the large projections 2 are distributed on the upper surface of the sleeping mat, and are uppermost protruded. Moreover, the top portions 2a are covered with a cover cloth 7 only. Therefore, when a large number of these top portions 2a are press-contacted with a human body, the top portions 2a can give an effective manual pressure effect to every contacted portions of the human body.

Further, the upper surface of the second fibrous sheet 5 is positioned at a level a little lower than the level of these top portions 2a, and the permanent magnets 6 are distributedly embedded in the second fibrous sheet 5, and the upper surface of the permanent magnet 6 is also covered with a cover cloth 7 only. Therefore, the permanent magnet 6 can give an effective magnetic effect to a human body without the weakening of its magnetic force.

Moreover, that portion of the laminated assembly consisting of the board 1 and the first and second fibrous sheets 4 and 5 which surrounds the projections 2 and magnets 6 is covered with a two-layered arrangement of first and second fibrous sheets 4 and 5 superposed of a large number of the small projections 3, and therefore the magnetic sleeping mat of the present invention is soft to the touch and further has excellent heat insulating properties. Furthermore, there are vacant spaces S, each having a sufficiently large dimension, between the bottom surface of the first fibrous sheet 4 and the upper surface of the board 1, which constitutes an interlining of the magnetic sleeping mat of the present invention (refer to FIGS. 9-11), and hence the magnetic sleeping mat has a high air permeability, is free from the stuffiness and further has a comfortableness as bedclothes.

Further, when a cloth 8, which has previously been subjected to a heat-insulation treatment or to a radiation heat-reflection treatment, such as vapor deposition of aluminum, or the like, is arranged between the lower first fibrous sheet 4 and the upper second fibrous sheet 5, the heat insulating property of the magnetic sleeping mat is more improved.

What is claimed is:

1. A magnetic sleeping mat, comprising a board consisting of a foamed synthetic resin; a first fibrous sheet superposed on the foamed synthetic resin board; a second fibrous sheet superposed on the first fibrous sheet; permanent magnets distributedly arranged on the second fibrous sheet; and a cover cloth which covers the laminated assembly consisting of the foamed synthetic resin board, the first fibrous sheet and the second fibrous sheet containing the permanent magnets; said foamed synthetic resin board having large projections, which are distributedly formed on its upper surface, and small projections, which are distributedly formed on its upper surface and are located between the large projections, and further having small projections, which are distributedly formed on its bottom surface; said first fibrous sheet having holes, which have been formed therethrough, and being superposed on the upper surface of the foamed synthetic resin board so as to be fitted in its holes with the large projections of the foamed synthetic resin board and to be contacted with the top portions of the small projections thereof; and said second fibrous sheet having holes, which have been formed therethrough, and being superposed on the upper surface of the first fibrous sheet so as to be fitted in its holes with the large projections of the foamed synthetic resin board.

2. A magnetic sleeping mat according to claim 1, which further comprises a cloth interposed between the lower first fibrous sheet and the upper second fibrous sheet, said cloth having previously been subjected to a heat insulation treatment or a radiation heat-reflection treatment.

* * * * *